United States Patent [19]

Ibnusaud et al.

[11] Patent Number: 6,147,228

[45] Date of Patent: Nov. 14, 2000

[54] CONVENIENT METHOD FOR THE LARGE SCALE ISOLATION OF GARCINIA ACID

[75] Inventors: Ibrahim Ibnusaud; Tom Thomas Puthiaparampil; Beena Thomas, all of Kottayam, India

[73] Assignee: Department of Science and Technology Government of India, India

[21] Appl. No.: 09/365,301

[22] Filed: Jul. 30, 1999

[30] Foreign Application Priority Data

Aug. 3, 1998 [IN] India ................................ 2248/Del/98

[51] Int. Cl.[7] .................................................. C07D 307/33

[52] U.S. Cl. .................................................. 549/318
[58] Field of Search .............................................. 549/318

[56] References Cited

U.S. PATENT DOCUMENTS 3,993,667  11/1976  Guthrie ................................. 260/343.6
5,536,516   7/1996  Moffett et al. ........................... 426/271

*Primary Examiner*—Amelia Owens
*Attorney, Agent, or Firm*—Londa & Gluck LLP

[57] ABSTRACT

A process for the isolation of Garcinia acid from the fresh or dried rinds of the fruits of *Garcinia indica, Garcinia cambogia* and/or *Garcinia atroviridis*.

11 Claims, 3 Drawing Sheets

I
Ia: R = H
Ib: R = CH₃
Ic: R = C₂H₅
Ic: R = C₂C₆H₅

Scheme I $^{13}$C nmr spectrum : δ 174.03, 171.06, 168.3, 84.06, 79.06 and 39.83 ppm. (in DMSO-d$_6$).

Mass spectrum : m/z 191(M+1)(2), 173(1), 162(6), 145(35), 127(10), 116(48), 99(70), 88(100), 60(40), 55(20).

CONVENIENT METHOD FOR THE LARGE SCALE ISOLATION OF GARCINIA ACID

BACKGROUND OF THE INVENTION

This invention is related to an improved and efficient process for the large-scale isolation of (−)-hydroxycitric acid or Garcinia acid (2S,3S-dihydroxy 1,2,3-propanetricarboxylic acid) from fresh or dried rinds of the fruits of *Garcinia cambogia, Garcinia indica* and *Garcinia atroviridis*. Garcinia acid is widely used as an important ingredient in many pharmaceutical formulations.

REFERENCES

1. U.S. Pat. No. 4,005,086 dated Jan. 25, 1977;
2. U.S. Pat. No. 4,006,166 dated Feb. 1, 1977;
3. U.S. Pat. No. 4,007,208 dated Feb. 8, 1977;
4. U.S. Pat. No. 5,536,516 dated Jul. 16, 1996;
5. U.S. patent No. WO9605741 A1 960229;
6. U.S. patent No. WO 9636585 A1 961121;
7. CA 86, 1977, 186629r;
8. CA 85, 1976, 41531x;
9. CA 87, 1977, 195626k;
10. CA 96, 1982, 30421n). The compound can be used as a potential precurser for the syntheses of many optically active natural products.

References a. Tetrahedron Letters Vol. 25 pp. 4491–4494, 1984;
b. Tetrahedron Vol. 43, No. 19, pp 4497–4506, 1987;
c. Tetrahedron Vol. 38, No. 15, pp 2377–2394, 1982;
d. Tetrahedron Vol. 34, pp 1449–1452, 1978;
e. J. Org. Chem. 63, 2385–2388, 1998;
f. JCS Chem. Comm. pp 711, 1973; 7.
g. Org. Chem. 58, 2725–2737, 1993;
h. Tetrahedron Vol. 31, pp 3011–3012, 1975;
i. Tetrahedron Letters Vol. 22, No. 52, pp 5271–5274, 1981;
j. Tetrahedron Letters Vol. 23 No. 48 pp 5051–5054, 1982).

However Garcinia acid, in the optically pure form, is not available in the market. This has resulted in the limited use of this compound in the synthetic front. The non-availability of this compound in the open market is due to the absence of any commercially viable large-scale manufacturing process. The present method describes an economic, commercially viable, cost effective process for the large-scale isolation of Garcinia acid (Ia).

EXISTING METHODS a. The method described by Y. S. Lewis and S. Neelakantan (Phytochemistry Vol. 4, 1965, pages 619–625) involves autoclaving the dried rinds of the fruits of *Garcinia cambogia* with water followed by the concentration of the filtered extract. Two volumes of alcohol is added to the concentrate to remove pectin and the filtrate is neutralised with alkali. The heavy liquid separated is washed several times with 60% aqueous alcohol to get alkali salt of the acid. The aqueous solution of the alkali salt is then passed through cation exchange resin to get (−)-hydroxy citric acid. Eluent on concentration yields crude lactone of the acid which is dried on water bath for several hours before drying in a vacuum oven for ten hours at 100° C. Finally the product is kept in a desiccater for several days to get a crude crystalline mass which is recrystallised from ether.

b. U.S. Pat. No. 5,536,516 dated Jul. 16, 1996 provides a method for enriching the content of (−)-hydroxycitric acid by subjecting the crude Garcinia rind extract to ion-exchange chromatography.

c. U.S. Pat. No. 5,656,314 and Patent No. WO 9605741 A1 960229 describes the preparation of a mixture of (−)-hydroxycitric acid, its lactone and citric acid.

d. The method reported by Per. M. Boll, Else Sorensen and Erik Balieu (Acta Chem. Scand 23 pp. 286–293, 1969) for the synthesis of Garcinia acid is a synthetic procedure. This involves oxidation of trans-aconitic acid using silver chlorate and osmium tetroxide followed by purification of the reaction mixture by preparatory layer chromatography in the milligram-scale. The oily material obtained is dried over $P_2O_5$ and recrystallised.

DRAWBACKS OF PRIOR ARTS

The main drawbacks of the existing method "a" are as follows.
1. It employs expensive tedious ion-exchange chromatography.
2. It is useful only for preparations in the milligram or gram scale.
3. Crystallisation of the product takes several days.
4. It is not at all suitable for large-scale isolation of the compound.

The drawbacks of the existing method "b" are listed below.
1. This method only enriches the content of (−)-hydroxycitric acid in Garcinia rind extract. It does not provide any means for the isolation of (−)-hydroxycitric acid lactone crystals.
2. It is suitable only for milligram or gram scale preparations.

The drawbacks of the existing method "c" are listed below.

Existing method "c" describes only a method for preparing a concentrate containing (−)-hydroxycitric acid, its lactone and citric acid. This does not provide a process for the isolation of pure Garcinia acid.

The drawbacks of existing method "d" are given below.
1. This method cannot be scaled up.
2. It involves the use of very expensive reagents.

ADVANTAGES OF THE NEW PROCESS

Principally the present invention is totally an alternative method for the isolation of Garcinia acid avoiding ion-exchange chromatography.

This process provides a simple and inexpensive method of obtaining crystals of Garcinia acid in the optically pure form, from natural sources.

The process is more efficient than all listed previous methods and it involves the use of cheap and reusable solvents, simple extraction methods and is less time consuming.

This method can be used for the production of Garcinia acid in the large scale. Crystallisation procedure described here is very fast and simple.

This assumes importance considering the potential of this compound in the pharmaceutical as well as synthetic front.

BRIEF DESCRIPTION OF THE DRAWINGS

FIG. 3 shows the mass 13-C nmr and mass spectrometry data for Garcinia acid of the invention.

DETAILED DESCRIPTION OF THE NEW INVENTION

Figure 1:
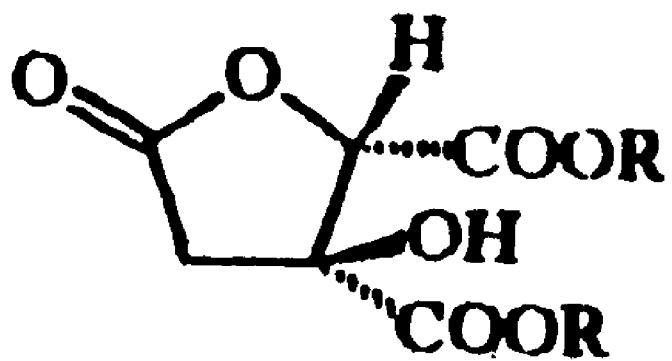
FIG. 1 is chemical formula showing Garcinia acid and homologs thereof.
Figure 2:
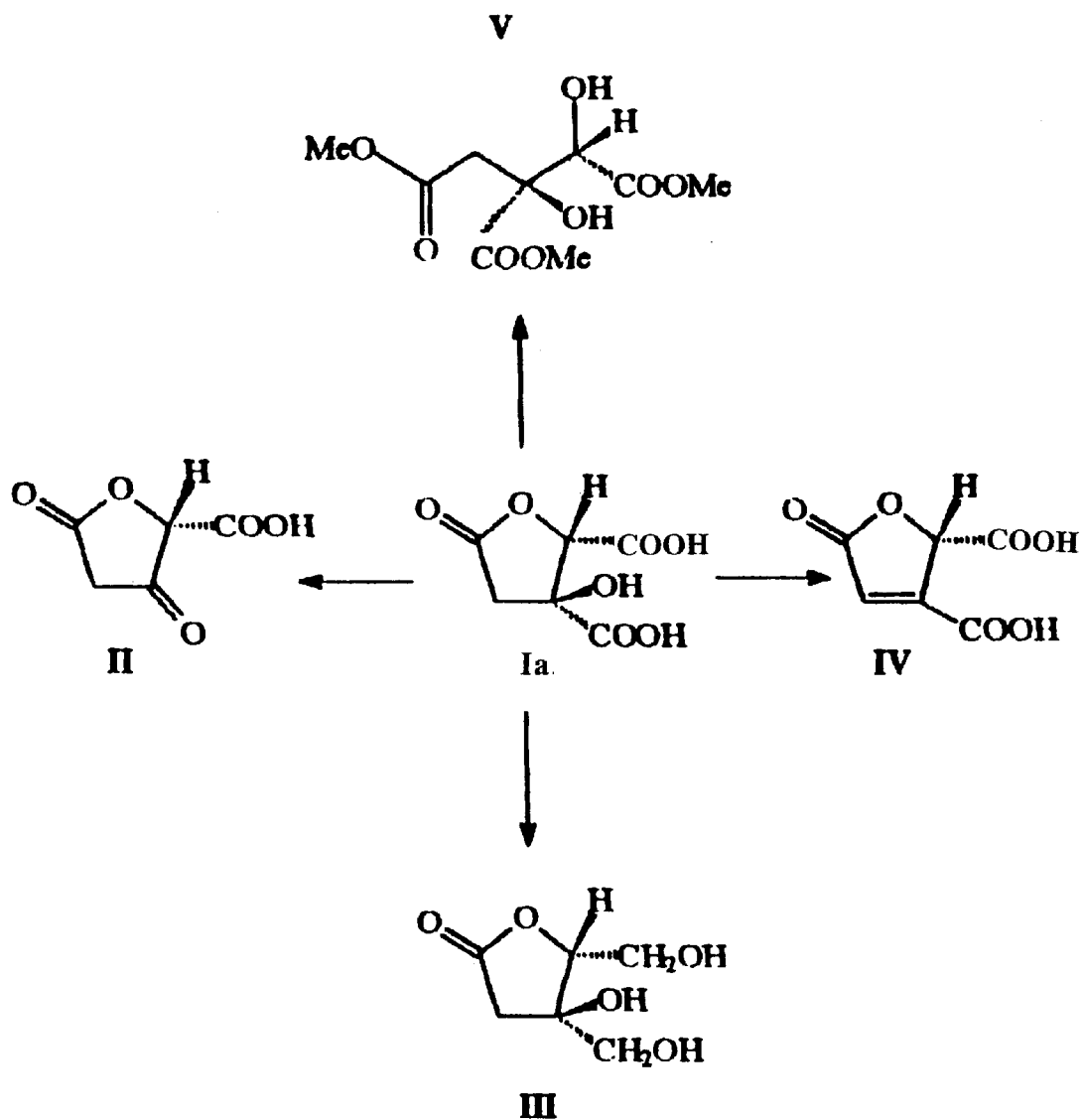
FIG. 2 shows the chemical formula of Garcinia acid, and formula for compositions derived as reaction products thereof.

The present invention involves the following steps.
1. The dried or fresh rinds of the fruits of *Garcinia cambogia*, *Garcinia indica* or *Garcinia atroviridis* are cut into small pieces and soaked in boiling water for 10–20 hours. The water extract is collected. The extraction is repeated a few times. The combined extracts are evaporated to a syrup (A). The soaking for longer time is avoided when fresh fruits are used. The water extract is also prepared by autoclaving the fresh or dried fruits.
2. To the syrup (A), sufficient quantity of alcohols like methanol, ethanol or butanol is added to remove pectin completely. The filtrate is concentrated to a syrup (B). Alternatively the fruit rinds are subjected to exhaustive soxhlet extraction using alcohols like methanol, ethanol or butanol to get pectin free extract. Recovered solvent is preserved for use at a later stage of the process.
3. After making syrup (B) alkaline by adding sufficient quantity of alkali at elevated temperature, alcohols like methanol, ethanol or butanol is added to the solution. Separated thick syrup (lower layer) is washed several times with aqueous alcohols like methanol, ethanol or butanol of varying proportions to get a paste of alkali salt (C). Recovered alcohol from step 2 is used for preparing aqueous alcohol.
4. The alkali salt (C) is neutralised with a mineral acid like hydrochloric acid and is evaporated to get a concentrate (D).
5. The concentrate (D) is triturated with sufficient quantity of an organic solvent like acetone, ether or methanol to precipitate inorganic matter and the filtrate upon concentration yielded crude Garcinia acid (E).
6. The crude acid (E) up on recrystallisation from solvents like acetone, methanol, ethanol, chloroform dichloroethane or their appropriate mixtures gives pure crystals of Garcinia acid (Ia). Yield is 5–10% of the weight of the dried fruit rinds. The purity of the product is confirmed by spectroscopic data and other physical data. The values of IR spectrum, melting point and optical rotation are comparable with the reported data.

The reported proton nmr values of Garcinia acid dates back to 1969. We have observed some anomalies in the proton nmr spectrum reported for the compound. The observed and reported values are given below.

used for $^{13}C$ nmr spectrum was a Brucker AMX 400 (400 MHz) spectrometer.

$^{13}C$ nmr spectrum: δ 174.03, 171.06, 168.3, 84.06, 79.06 and 39.83 ppm. (in DMSO-$d_6$).

Mass spectrum: m/z 191(M+1) (2), 173 (1), 162 (6), 145 (35), 127 (10), 116 (48), 99 (70), 88 (100), 60 (40) and 55 (20).

Functionalised furanones (Scheme I) are important building blocks in organic synthesis. These lactones are useful for the preparation of optically active ligands and for the synthesis of biologically active natural products. Garcinia acid (Ia) isolated by the present method was effectively used for the preparation of Ib, Ic, Id, II, III, IV and V (Scheme I). These compounds were synthesised by the reaction of title compound (Ia).

with methanol and acid (Ib),
with ethanol and acid (Ic),
with benzylalcohol and acid (Id),
with oleium (II),
with $BH_3$-THF (III),
with HBr followed by elimination (IV)
with HBr in methanol (V)

The process of the invention is illustrated by the following example which should not be construed to limit the scope of the present invention.

EXAMPLE

Dried rinds of the fruits of *Garcinia cambogia* (2.0 Kg) were cut into small pieces and were soaked in boiling water for 20 hours. Extract was collected and the process was repeated 4–5 times. The combined extracts were concentrated to get a thick mass and methanol was added. Pectin was filtered off and the filtrate was concentrated to a syrup. Recovered methanol was preserved use at a later stage. The syrup was made alkaline by adding sufficient quantity of aqueous sodium hydroxide solution at about 80° C. and recovered methanol was added till two layers separated. The lower layer which contained the sodium salt of Garcinia acid was washed several times with about 50% aqueous methanol, prepared from recovered methanol. The pure sodium salt was neutralised with hydrochloric acid was concentrated. Acetone was added and inorganics were filtered off. The filtrate on concentration yielded crude crystals of Garcinia acid, the crude lactone was recrystallised from acetone-chloroform mixture to give pure crystals of the compound (Ia).

Melting point: 178° C. Yield: 135.0 g The specific rotation was recorded on a Roudolf polarimeter. $[\alpha]^D_{20}$: 102.151 deg.

| $^1H$ nmr | Instrument used | $_\alpha C$ | | | | $_\beta C$ | | $_xC$ | |
|---|---|---|---|---|---|---|---|---|---|
| | | $H_A$ | $H_B$ | OH | COOH | H | | COOH | |
| Reported value (in DMSO-$d_6$) | Varian A 60A | 3.07(d) | 3.51(d) | — | — | 9s)4.71 | | — | |
| Observed value (in acetone-$d_6$) | Brucker AMX 400 (400 MHz) | 2.60(d) | 3.07 d) | — | — | (s)4.80 | | — | |

Literature survey reveals that there are no data available on $^{13}C$ nmr spectrum and mass spectrum of Garcinia acid. We have recorded $^{13}C$ nmr spectrum and mass spectrum of the compound and the values are given below. Instrument

What is claimed is:
1. A process for the isolation of Garcinia acid from the fresh or dried rinds of the fruits of *Garcinia indica*, *Garcinia cambogia* and/or *Garcinia atroviridis*, comprising the steps of, in sequence:

(a) subjecting the rinds to extraction to form an extract (b) adding a solvent to the extract to remove pectin and form a filtrate (c) converting the filtrate to form an alkali salt (d) neutralizing the alkali salt with an acid, followed by evaporation, to form a concentrate (e) purifying said concentrate using a solvent to remove inorganic matter as impurities, to form a second filtrate (f) concentrating the second filtrate to yield a crude Garcinia acid (g) recrystallizing the crude to form pure crystals of Garcinia acid.

2. The process of claim 1, wherein step (a) is repeated a plurality of times, each with a new batch of rinds, to provide a plurality of extract batches, said batches being combined and concentrated to form a thick syrup.

3. The process of claim 1, wherein in step (a), the rinds are cut into small pieces and soaked in boiling water for 10–20 hours to effect the extraction.

4. The process of claim 1, wherein in step (a), the extraction comprises a soxhelt extraction with a solvent chosen from the group consisting of methanol, ethanol and butanol.

5. The process of claim 1, wherein the water extract is prepared by autoclaving the rinds.

6. The process of claim 1, wherein in step (b), the solvent is chosen from a group consisting of methanol, ethanol and butanol.

7. The process of claim 5, wherein step (c) comprises concentrating the filtrate, adding an alkali to the filtrate so that the filtrate becomes alkaline, adding an alcohol to the alkaline filtrate to form an upper and lower layer, separating said lower layer and washing with an aqueous alcohol to form an alkali salt paste.

8. The process of claim 1, wherein in step (e), the concentrate is triturated with a solvent chosen from the group consisting of acetone, ether and methanol.

9. The process of claim 1, wherein in step (g), a solvent is used to effect recrystallization, the solvent being chosen from the group consisting of acetone, methanol, ethanol, chloroform and dichloroethane.

10. Garcinia acid in optically pure, crystal form.

11. The garcinia acid of claim 10, having carbon-13 NMR and mass spectral data substantially as shown in FIG. 3.

* * * * *